(12) United States Patent
Doccola et al.

(10) Patent No.: US 9,873,639 B1
(45) Date of Patent: Jan. 23, 2018

(54) AGRICULTURAL BIOMASS AS A MATRIX FOR RELEASE OF PLANT ACTIVE COMPOUNDS

(71) Applicants: Joe Doccola, Brentwood, NH (US);
Russell Davis, Jr., Lynnfield, MA (US);
Srdan G Acimovic, Woburn, MA (US);
Don Grosman, Pelham, NH (US)

(72) Inventors: Joe Doccola, Brentwood, NH (US);
Russell Davis, Jr., Lynnfield, MA (US);
Srdan G Acimovic, Woburn, MA (US);
Don Grosman, Pelham, NH (US)

( * ) Notice: Subject to any disclaimer, the term of this patent is extended or adjusted under 35 U.S.C. 154(b) by 39 days.

(21) Appl. No.: 14/802,488

(22) Filed: Jul. 17, 2015

(51) Int. Cl.
| | |
|---|---|
| *A01N 43/50* | (2006.01) |
| *A01N 25/08* | (2006.01) |
| *C05G 3/00* | (2006.01) |
| *C05G 3/02* | (2006.01) |
| *C05C 11/00* | (2006.01) |
| *C05G 3/04* | (2006.01) |
| *C09K 17/02* | (2006.01) |

(52) U.S. Cl.
CPC ........... *C05G 3/0047* (2013.01); *A01N 25/08* (2013.01); *A01N 43/50* (2013.01); *C05C 11/00* (2013.01); *C05G 3/0082* (2013.01); *C05G 3/02* (2013.01); *C05G 3/04* (2013.01); *C09K 17/02* (2013.01)

(58) Field of Classification Search
None
See application file for complete search history.

(56) References Cited

FOREIGN PATENT DOCUMENTS

| | | | |
|---|---|---|---|
| CN | 102417423 | * | 4/2012 |
| CN | 103483107 | * | 1/2014 |
| CN | 10423525 | * | 12/2014 |
| CN | 104193501 | * | 12/2014 |

OTHER PUBLICATIONS

Olson et al., Ecological Letters, 2014, 17: 988-997.
Sperry et al., American Journal of Botany. 2006, 93(10): 1490-1500.
Yu, X. et al., Chemosphere (2009) 76: 665-671).

* cited by examiner

*Primary Examiner* — Alton Pryor
(74) *Attorney, Agent, or Firm* — Naomi S. Biswas; Patent GC

(57) ABSTRACT

The invention is directed to compositions comprising at least one agricultural biomass, at least one nitrogen source, at least one organic acid and at least one active agent wherein the agricultural biomass is impregnated with about 5% wt to about 45% wt of the active agent. Methods of their preparation and methods of use are also described. The composition effectively reduces the leaching of, and facilitates the metering of, loaded active agents for plant protection.

17 Claims, No Drawings

AGRICULTURAL BIOMASS AS A MATRIX FOR RELEASE OF PLANT ACTIVE COMPOUNDS

FIELD OF THE INVENTION

The present invention relates to agricultural biomass compositions, including biochar, and their use as a matrix for the controlled or immediate release of plant active compounds. Methods of their preparation and methods of use are also described.

BACKGROUND OF THE INVENTION

The challenge in agrochemistry or other large scale field applications of chemicals or active agents such as, for example, pesticides, herbicides, bacteriocides, nematicide and fungicides is to find ways of achieving control of the target organism while limiting the amount of the xenobiotic substance that is loaded into and is free-moving in the ecosystem by leaching or by aerosol drift. The amount of such chemical that is required is a function of their potency, the ability to place the chemical selectively and their susceptibility to removal either via destruction in the environment (metabolism, photolysis, etc.) or loss (leaching, drift). Unfortunately, environmentally desirable properties such as facile biodegradation or other loss may result in a need for frequent re-application and thus an increase in the load on the environment. Although there has been dramatic progress in identifying more potent active agents for use in pest control there has been rather less success in controlling the application or placing of these chemicals in such a way as to limit losses and maximize efficacy.

When a chemical is applied to soil, it does not always stay put. Chemicals follow any number of pathways. They can enter plants, insects, and other living organisms. They can volatilize, which means they change into a gas. They can be broken down by sunlight, microorganisms, or chemical reactions with water, and they can chemically attach to soil and organic particles. They can also remain in a dissolved form, and then leach with water through the soil, sometimes winding up in groundwater. The fate of mobile chemicals, however, can be thought of as a race between the various degradation processes and leaching to groundwater. Leaching is the movement of contaminants, such as water-soluble pesticides or fertilizers, carried by water downward through permeable soils. Generally speaking, most pesticides adsorb to soil particles (especially clay), become immobile, and do not leach. The fate of mobile pesticides, however, can be thought of as a race between the various degradation processes and leaching to groundwater. In contrast to surface water, groundwater does not continually dilute the contaminants that reach it. Flushing a plume of contamination from groundwater may take many years. The cold temperatures, limited microbiological activity, lack of sunlight and low oxygen levels that are found deep beneath the soil surface, slow chemical breakdown. The result is that there is very little, if any, breakdown of chemicals once they reach an aquifer.

As mentioned above, chemicals often do not reach their intended target but are transported to groundwater and surface waters. There is a need in the art for improved retention and release (controlled application) of active agents for agriculture in a manner that reduces loss of actives to leaching. The invention is directed to these, as well as other, important ends.

SUMMARY OF THE INVENTION

Biochar is increasingly being recognized by scientists and policy makers around the globe for its potential role in carbon sequestration, reducing greenhouse gas emissions, renewable energy, waste mitigation, and as a soil amendment. Studies have shown that incorporation of biochars in soil could directly reduce the bioavailability of pesticides in soils, and thus can significantly reduce their plant uptake (Xiang-Yang Yu et al., Chemosphere (2009) 76: 665-671). However Applicants have discovered that surprisingly agricultural biomass, such as biochar, can be used as a matrix for the release of plant active compounds. The addition of hygroscopic substances onto biochar function to retain and draw moisture to the root zone to enhance plant establishment, growth and to reduce drought induced stress. The invention thus discloses an agricultural biomass composition comprising at least one plant active agent for the controlled release or the immediate release of the plant active agent.

One embodiment of the invention features a composition comprising at least one agricultural biomass, at least one nitrogen source, at least one organic acid and at least one active agent wherein the agricultural biomass is impregnated with about 5% wt to about 45% wt of the active agent. In other embodiments, the agricultural biomass is impregnated with active ingredient ranging from about 5-10%, 10-15%, 15-20%, 20-25%, 25-30%, 30-35%, 35-40%, or 40-45% wt. In one specific embodiment the composition comprises a biochar agricultural biomass component comprising about 5% wt to about 75% wt of an herbaceous, non-woody and/or monocot biochar or a hardwood biochar or a softwood biochar or a combination one or more thereof. In another embodiment the biochar comprises about 25% wt to about 50% wt (including the ranges of between about 25-30%, 30-35%, 35-40%, 40-45%, and 45-50%) of a herbaceous, non-woody, monocot biochar, and about 50% wt to about 75% wt (including the ranges of between about 50-55%, 55-60%, 60-65%, 65-70%, and 70-75%) of a hardwood biochar. In one embodiment, the biochar agricultural biomass component comprises between abut 25-75% by weight of the composition. In other embodiments, the agricultural biomass composition comprises from about 25-30%, 30-35%, 35-40%, 40-45%, 45-50%, 50-55%, 55-60%, 60-65%, 65-70% or 70-75% by weight of the composition.

In another embodiment of the invention, the composition has a bulk density of less than about 40 pounds per cubic foot and has a size of about 90-100%, more preferably 95-100%, and even more preferably 98-100% passing through a ¼" mesh screen and about 50% or more passing through a 4 mesh screen; or a size of about 90-100%, more preferably 95-100%, and even more preferably 98-100% passing through a No. 4 mesh screen and about 70% or more passing through a No. 10 mesh screen; or a size of about 90-100%, more preferably 95-100%, and even more preferably 98-100% passing through a No. 10 mesh screen and about 50% or more passing through a No. 45 mesh screen.

In one embodiment of the invention, the agricultural biomass is impregnated with about 5% wt to about 45% wt of an active agent, including the ranges of from about 5-10%, 10-15%, 15-20%, 20-25%, 25-30%, 30-35%, 35-40%, or 40-45% wt. In this embodiment the active agent any agent that regulates plant growth, and can be selected from an insecticide, an insect growth regulator, a fungicide, a plant growth regulator, a pesticide, an algicide, a bacteriocide, a defoliant, a herbicide, a miticide, a nematicide, an ovicide, a pheromone, a repellent, a bio-pesticide, a fertilizer, an hygroscopic substance or a pest reproductive control agent or a combination of two or more thereof.

In yet another embodiment of the invention, the agricultural biomass is impregnated with an insecticide, an insect growth regulator, a fungicide, a plant growth regulator, or a bio-pesticide. In certain embodiments of the invention the insecticide is imidacloprid, dinotefuran, acephate or abamectin; the insect growth regulator is azadirachtin; the fungicide is thiabendazole, triadimefon or a strobulurin (e.g., azoxystrobin, trifloxystrobin); the plant growth regulator is paclobutrazol, ethephon or auxin (e.g., IAA, indole-3-butyric acid, NAA); and the bio-pesticide is spinosad (a mixture of spinosad A and spinosad D).

In another embodiment, the composition comprises a nitrogen source selected from blood meal, bone meal, kelp meal, sodium nitrate, sulfur-coated urea, inorganic salts such as, for example, magnesium ammonium nitrate, potassium nitrate, ammonium nitrate, calcium nitrate, and the like; urea-formaldehyde reaction products, and isobutylidene diurea (IBDU), or a combination of two or more thereof.

In another embodiment, the composition comprises an organic acid selected from calcium chelate derived from calcium chloride, 5% chelated iron derived from iron sulfate, 5% manganese chelate derived from manganese sulfate, 5% zinc chelate derived from zinc sulfate; alternatively, copper (II) sulfate pentahydrate, boric acid, phosphoric acid, and sodium molybdate or a combination of two or more thereof.

In one embodiment the composition comprising at least one agricultural biomass, at least one nitrogen source, at least one organic acid and at least one active agent releases the active agent from the agricultural biomass in a controlled release manner.

In another embodiment the composition comprising at least one agricultural biomass, at least one nitrogen source, at least one organic acid and at least one active agent releases the active agent from the agricultural biomass immediately.

In yet another embodiment the composition comprising at least one agricultural biomass, at least one nitrogen source, at least one organic acid and at least one active agent releases a portion of the active agent from the agricultural biomass immediately and the remainder of the active agent from the agricultural biomass in a controlled release manner.

In yet another embodiment the composition which comprises an agricultural biomass composition impregnated with about 5% wt to about 45% wt of an active agent releases the active agent at a rate in the range of from about 10 mg/L to about 500 mg/L. In a preferred embodiment, the release rate is about 33 mg/L.

In one specific embodiment, the composition comprises about 46% wt biochar as the agricultural biomass, about 10% wt chelated calcium chloride as the organic acid, about 34% wt blood meal as the nitrogen source, and about 10% wt technical imidacloprid as the active agent.

In yet another embodiment, the composition comprises an agricultural biomass of biochar consisting of about 5% wt to about 75% wt of an herbaceous non-woody monocot biochar or a hardwood biochar or a softwood biochar or a combination one or more thereof, at least one nitrogen source, at least one organic acid and at least one active agent present from about 5% wt to about 45% wt of the composition. The biochar composition has a bulk density of less than about 40 pounds per cubic foot and has a size of about 100% passing through a ¼" mesh screen and about 50% or more passing through a 4 mesh screen; or a size of about 100% passing through a No. 4 mesh screen and about 70% or more passing through a No. 10 mesh screen; or a size of about 100% passing through a No. 10 mesh screen and about 50% or more passing through a No. 45 mesh screen. The composition has a bulk density of less than about 40 pounds per cubic foot with <20% wt moisture.

Another aspect of the invention provides methods of making the composition and its methods of use. In one embodiment the agricultural biomass of appropriate size is blended with a nitrogen source and an organic acid. The resulting mixture is then loaded with the active agent by adding a concentrated solution of the active agent followed by tumbling to evenly distribute the active agent on to the agricultural biomass composition, then drying to specified moisture content. In another embodiment the active agent in powder form is optionally intermixed with the agricultural biomass. Without intending to be bound to a particular theory, electrostatic forces are believed to be operative to retain active agent powder in contact with the granules of the agricultural biomass. The resulting agricultural biomass composition impregnated with the active agent effectively reduces the leaching of and facilitates the metering of the active agent. The composition is administered volumetrically (teaspoon, tablespoon, cup, shaker, spreader), or by weight (biodegradable packet) or by soil implantation with an insertion tool to an environmental area comprising the soil or root zone in which plants grow, typically within the top 12" of the soil surface. The composition may optionally be applied to the root ball from which roots are expected to emerge upon planting.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

DETAILED DESCRIPTION OF CERTAIN PREFERRED EMBODIMENTS OF THE INVENTION

As used throughout the disclosure, the following terms, unless otherwise indicated, shall be understood to have the following meanings.

Definition/Terminology

The use of the articles "a", "an", and "the" in both the following description and claims are to be construed to cover both the singular and the plural, unless otherwise indicated herein or clearly contradicted by context. The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

"Agricultural biomass" as used herein means any cellulosic or lignocellulosic plant material, especially waste material, including but not limited to, leaves, stalks, wood chips, barks, straw, stalks, husks, chaff and hulls of both woody and non-woody plants.

"Woody" is used herein both in the botanical sense to mean "comprising wood"; that is, composed of extensive xylem tissue as found in trees and shrubs, and also in the sense of "being wood-like". Accordingly, "non-woody" refers to materials lacking these characteristics.

"Impregnated" or "impregnate" as used herein refers to infused or permeated throughout or adsorbed. It refers to the occupation of a portion (e.g., about 20, 30, 40, 50, 60, 70, 80, 90, 99% or more of the space within the pore) of the porous structure of the agricultural biomass so that the active agent permeates the porous structure of the agricultural biomass.

"Active agent" as used herein refers to any plant active compound.

"About" as used herein is intended to mean, that a numerical value encompasses the typical variation in measuring the value, in an embodiment plus or minus 10% of the numerical value.

"Immediate release" as used herein refers to a composition that releases one or more of the active agents within a short period of time after administration of the composition. The immediate release profile of the composition can be determined by the dissolution profile of the active agents in vitro.

"Controlled release" as used herein refers to a composition that releases one or more of the active agents over an extended period of time after administration of the composition. The controlled release profile of the composition can be determined by the dissolution profile of the active ingredients in vitro.

Agricultural Biomass

In certain exemplary embodiments, the agricultural biomass of the invention derived from woody plants would include orchard pruning, chaparral, mill waste (such as bark, chips, shavings, sawdust, and the like), urban wood waste (such as discarded lumber, wood pallets, crates, tree and brush trimming, etc.), municipal waste (such as newspaper and discarded grocery produce), logging waste and forest thinning (tree tops, limbs and cull material), short-rotation woody crops such as poplar and cottonwood, and industrial waste (such as wood pulp sludge).

In certain exemplary embodiments, the agricultural biomass of the invention is biochar. Use of lower temperatures produces biochars with aliphatic arrangements of carbon, whereas at higher temperatures, aromatic carbon structures are produced. In some embodiments the softwood biochars are derived from gymnosperms which have very restricted vascular tissues comprised solely of tracheids. These tracheids range in width from 10 to 65 µm diameters. In other embodiments the hardwood biochar is derived from angiosperms that contain conductive tissues comprised of both vessels and tracheids. Vessels in hardwood trees range from 17 to 150 µm diameters (Sperry et al., American Journal of Botany. 2006, 93(10): 1490-1500). In tropical lianas (vines) vessels may be as large as 500 µm diameters (Zimmerman, M. H. 1983. Xylem structure and the ascent of sap. Springer-Verlag. Berlin, Germany). Monocots tend to have vessel diameters ranging from 25 to 250 µm (Olson et al., Ecological Letters, 2014, 17: 988-997). Vessel size plays a role in absorptive capacity of biochar, whereas size of granule changes the surface area upon which cations or molecules with a net positive charge may be adsorbed.

In certain exemplary embodiments, the preponderance of biomass from non-woody plants is derived from monocotyledonous plants, and especially grassy species belonging to the family Gramineae. Of primary interest are gramineous agricultural residues; that is, the portion of grain-bearing plants that remain after harvesting the seed. Illustrative of such residues, without limitation thereto, are wheat straw, oat straw, rice straw, barley straw, rye straw, flax straw, sugar cane, corn stover, corn stalks, corn cobs, corn husks, and the like. Also included within this definition are grasses not conventionally cultivated for agricultural purposes, such as bamboo, prairie grasses (e.g. big bluestem, little bluestem, Indian grass), gamagrass, and foxtail.

Other agricultural byproducts in the category of biomass useful for the invention include waste streams components from commercial processing of crop materials (such as sugar beet pulp, citrus fruit pulp, seed hulls, and the like), cellulosic animal wastes, lawn clippings, seaweed, etc.

In one specific embodiment the composition comprises an agricultural biomass ranging from about 25% wt to about 75% wt of the composition. In one embodiment, the agricultural biomass is herbaceous, non-woody and/or monocot. In another embodiment the agricultural biomass comprises a hardwood agricultural biomass or a softwood agricultural biomass or a combination of one or more thereof. In yet another embodiment the agricultural biomass component of the composition comprises about 25% wt to about 50% wt of an herbaceous, non-woody, monocot agricultural biomass and about 50% wt to about 75% wt of a hardwood agricultural biomass.

In one embodiment of the invention the agricultural biomass is biochar. Biochar is a charcoal created by the pyrolysis of biomass. Pyrolysis is a thermo-chemical decomposition of organic material at elevated temperatures, typically 450 to 500° C., in the absence of oxygen. It involves the simultaneous change of chemical composition and physical phase, and is irreversible. The end product has a porous (absorptive) and adsorptive surface with a large surface area, thereby providing structure for both the absorption and adsorption of active agents. The quality of biochar varies depending on the source and production process. A particular advantage of using biochar, that is a charcoal granule created by pyrolysis of biomass, is that the interaction of biochar not only constitutes a net carbon sequestration but also serves to adsorb, hold and variably release active agents.

In another embodiment the biochar comprises a hardwood biochar or a softwood biochar or a combination one or more thereof. In yet another embodiment the biochar comprises 25% wt to about 50% wt (including the ranges of between about 25-30%, 30-35%, 35-40%, 40-45%, and 45-50%) of an herbaceous, non-woody, monocot biochar and about 50% wt to about 75% wt (including the ranges of between about 50-55%, 55-60%, 60-65%, 65-70%, and 70-75%) of a hardwood biochar.

In yet another embodiment the biochar comprising a hardwood biochar or a softwood biochar or a combination one or more thereof provides a matrix for the adsorption of an active agent. In yet another embodiment the biochar comprising 25% wt to about 50% wt (including the ranges of between about 25-30%, 30-35%, 35-40%, 40-45%, and 45-50%) of a herbaceous, non-woody, monocot biochar and 50% wt to about 75% wt (including the ranges of between about 50-55%, 55-60%, 60-65%, 65-70%, and 70-75%) of a hardwood biochar provides a matrix for the adsorption of one or more active agents.

The biochar matrix provides a variable absorptive particle and surface area providing a high cationic exchange capacity (CEC). The particle size and holding capacity are inversely related. The sizing is optionally determined in accordance with ASTM D2862-10. Alternatively the size of the particles may be determined by the size guide number/uniformity index system that describes the relative particle size and is obtained by multiplying the average particle size, in millimeters, by 100. The uniformity index is a comparison of large particles to small particles. The index is expressed as a whole number between 1 and 100 with higher numbers indicating better uniformity and tighter size range.

In one embodiment the biochar is milled such that about 100% passes through ¼ " and 50% passes through a No. 4 mesh. In another embodiment, the biochar is milled such that about 100% of the biochar passes through a No. 4 mesh screen and about 80% or more passes through a No. 10 mesh screen. In yet another embodiment the biochar is milled such that about 100% of the biochar passes through a No. 10 mesh and 50% passes through a No. 45 mesh.

Active Agents

The active agents used in the invention include insecticides, insect growth regulators, fungicides, plant growth regulators, pesticides, pheromones, repellents, bio-pesticides, hygroscopic substances or pest reproductive control agents or a combination of two or more thereof.

Exemplary insecticides include neonicotinoids, such as acetamiprid, clothianidin, imidacloprid, dinotefuran and thiamethoxam; organophophates such as, acephate, diazinon, dimethoate, methamidophos, and phorate; glycosides such as abamectin and its derivatives, such as for example, emamectin benzoate; and botanicals such as azadirachtin, cavacrol, d-limonene, nicotine, pyrethrins, rotenone, ryania, and sabadilla; inorganic insecticides, such as boric acid, calcium polysulfide, and copper oleate; pyrazoles such as chlorantraniliprole, cyantraniliprole and cyclaniliprole, and butenolides, such as flupyradifurone.

Exemplary insect growth regulators include azadirachtin, chitin synthesis inhibitors, such as cyromazine, benzoylphenylurea chitin synthesis inhibitors such as, chlorbenzuron, flucycloxuron, hexaflumuron, novaluron, and triflumuron; juvenile hormone mimics such as, fenoxycarb, kinoprene, and pyriproxyfen; juvenile hormones; moulting hormone agonists, such as furan tebufenozide, halofenozide, and methoxyfenozide; moulting hormones, such as α-ecdysone, and ecdysterone; moulting inhibitors such as diofenolan, and the procecenes.

Exemplary fungicides include propiconazole, thiabendazole, triadimefon or a strobulurin, such as, for example, azoxystrobin and trifloxystrobin; aliphatic nitrogen fungicides, such as butylamine; amides, such as fenoxanil and prochloraz; acylamino fungicides, such as metalaxyl; analide fungicides, such as, vangard, benzanilides, such as, salicylanide; furanilides such as methfuroxam; sulfanilides such as flusulfamide; benzamides such as benzohydroxamic acid and fluopyram; furamides such as furmercyclox; phenylsulfamides, such as dichlofuanid; sulfonamides such as cyazofamid; valinamides, such as iprovalicarb; strobilurin fungicides such as fluoxastrobin, azoxystrobin, pyraoxystrobin and trifloxystrobin; aromatic fungicides such as, chlorthalonil, cresol and pentachlorophenol; benzimidazoles such as benomyl, debcarb, thiabendazole, and thiophanate-methyl; botanical fungicides, such as berberine, carvacrol, carvone, osthol, sanguinarine, and santonin; conazole fungicides, such as cyproconazole, difenoconazole, propiconazole, tebuconazole, tetraconazole, triadimefon, triconazole and uniconazole; copper fungicides, such as Bordeaux mixture, copper carbonate (basic), copper hydroxide, copper oleate, copper oxychloride, copper sulfate, and cuprous oxide; phthalimides, such as captan and folpet; dithiocarbamates such as ferbam, thiram, ziram, mancozeb, maneb and zineb; sulfur; polysulfides such as, calcium polysulfide, and potassium polysulfide; quaternary ammonium fungicides such as beberine, and sanguinarine; thiazoles anf thiocarbamates such as, zinc thiazole, and prothiocarb; urea fungicides, such as pencycuron and quinazamid; and zinc fungicides, such as cufraneb, propineb and ziram.

Exemplary plant growth regulators include, plant growth hormones, cytokinins, such as kinetin and zeatin; auxins, such as IAA, IBA, indole-3-butyric acid, α naphthaleneacetic acids; and gibberellins, such as gibberellic acid; ethylene, ethephon; growth inhibitors, such as, abscissic acid, ancymidol, dikegulac, maleic hydrazide, paclobutrazol; growth stimulators, such as pyripropanol, and triacontanol; or and a combination thereof.

Exemplary pesticides include algicides, such as copper sulfate, diuron, endothal, hydrated lime, isoproturon, oxyfluorfen, pentachlorophenyl laurate, and quinonamid; bacteriocides, such as copper hydroxide, cresol, kasugamycin, oxytetracycline, streptomycin, thiodiazole-copper, and zinc thiazole; defoliants, such as calcium cyanimide, endothal, pentachlorophenol and thidiazuron; herbicides, such as 2,3, 6-TBA, dicamba, picloram, cacodylic acid, triclopyr, ammonium sulfamate, borax, calcium chorate, copper sulfate, ferrous sulfate, potassium cyanate, sodium chlorate, sulfuric acid, 2,4-DEP, glyphosate, 2,4-D, 2,4,5-T, α-naphthaleneacetic acids and sodium naphthenate, diquat, paraquat, atrazine, simazine, amitrole, cycluron, dichlorurea, noruron. diuron, sulfosulfuron, trifloxysulfuron, allyl alcohol, cresol, endothal, and pelargonic acid; miticides, such as abamectin, azothoate. benzyl benzoate, bifenthrin, carvacrol, chlorpyrifos, demeton-methyl, fipronil, pyriminostrobin, spiromesifen, tetranactin, and sulfur; mite growth regulators, such as cyromazine, fluazuron, and flucyclouron; nematicides such as abamectin, emamectin benzoate, carvacol, benomyl, and phorate; or ovicides. Other suitable pesticides include, for example, pyrethroids such as bifenthrin, permethrin, deltamethrin, lambda cyhalothrin, or cyfluthrin; organophosphates such as, for example, acephate, chlorpyrifos or trichlorfon; pyrazoles such as, for example, fipronil; limonoids such as, for example, azadirachtin or meliartenin; avermectin insecticides, such as, for example, abamectin; anthranilic diamides, or spinosyns; neonicotinoids; nitroguanidines such as, for example, imidacloprid, thiomethoxam, clothianidin or dinotefuran; neonicotines such as, for example, floconamid; anthranilic diamides such as, for example, chlorantraniliprole or cyantraniliprole, and butenolides such as flupyradifurone.

Exemplary pheromones include acetosyringone, farnesene, farnesol, cis-3-hexen-1-ol, pyrrolizidine alkaloids, (s)-ipsdienol, (z)-9-tricosene, eugenol, methyl eugenol, verebone, brevicomin, frontalin, ipsdiendol, ipsenol, and trunc-call, rescalure, dispalure, hexalure and ostramone.

Exemplary repellents include azadirachtin, butopyronoxyl, camphor, citronella oil, d-camphor, dibutyl succinate, icaridin, neem oil, permethrin, quyingding, and zengxiaoan.

Exemplary bio-pesticides include spinosad (spinosad A and spinosad D) and phosphonate.

Exemplary hygroscopic substances include humectants, such as propylene glycol, glyceryl triacetate, sugar alcohols, Aloe vera, alpha hydroxyl acids, and polymeric polyols.

Exemplary pest reproductive control agents includes acaracides, such as abamectin, azothoate. benzyl benzoate, bifenthrin, carvacrol, chlorpyrifos, demeton-methyl, fipronil, pyriminostrobin, spiromesifen, tetranactin, and sulfur; mite growth regulators, such as cyromazine, fluazuron, and flucyclouron; antimicrobial compounds, bactericides, fungicides, synthetic plant growth regulators such as, for example, gibberellic acid synthesis inhibitors or promoters, insecticides, molluscicides, nematacides, pheromones, larvicides, ovicides, molting signaling compounds or steroids that upon contact with the target pest decreases the reproductive capacity of the pest.

In one embodiment, the active ingredient is an insecticide, an insect growth regulator, a fungicide, a plant growth regulator, or a bio-pesticide. In certain embodiments of the invention the insecticide is imidacloprid, dinotefuran, acephate or abamectin; the insect growth regulator is azadirachtin; the fungicide is thiabendazole, triadimefon or a strobulurin (e.g., azoxystrobin, trifloxystrobin); the plant growth regulator is paclobutrazol, ethephon or auxin (e.g., IAA, indole-3-butyric acid, NAA); and the bio-pesticide is spinosad (a mixture of spinosad A and spinosad D).

In one embodiment agricultural biomass can be impregnated with the active agent. The active agent can also be present on the surface of the agricultural biomass.

A blend of monocot, hardwood or softwood biochars may be selected in building the granular formulation. Monocot Char is desirable for use to internally load (process of absorption) actives with relatively low carbon adsorption coefficients (Koc), based on their larger porosity (on the order of 250 µm) whereas other biochars (for example, those derived from hardwood or softwood sources, which are less porous, i.e., 150 to 10 µm, respectively) may be used for actives which have moderate to high carbon adsorption coefficients, respectively, held externally (process of adsorption) onto the char particle. To increase adsorption (external loading), mill sizes are selected in the range of 2000 to 4760 µm. To increase the internal loading (absorption), biochar with larger porosity is selected. It may be desirable to mill monocot biochar larger, i.e., from 6350 to 4760 µm size. Biochars which have lower density (higher porosity) are selected for low Koc molecules, which more readily leach. To create blends of actives, for example, a fungicide and insecticide or to blend actives with different adsorption coefficients, two type of biochars (monocot and hardwood or softwood) are required. It is conceivable, then to blend chars from different sources milled to the same, overlapping or different size grades and load onto it actives of various Koc into a blended formulation. In so doing, one can further refine the sorption-desorption characteristics for timed release of the active(s). For example, actives such as dinotefuran which have relatively high water solubility and low Koc is loaded onto char with high porosity (i.e., monocot char) to facilitate internal loading (impregnation). Alternately, acephate is likewise first solubilized, then internally loaded to increase retention. The systemic activity of dinotefuran and acephate is well documented, and these, placed into roots will act upon insects feeding on the above ground plant tissues (such as leaves and stems). In contrast, molecules with high carbon adsorption coefficients are externally loaded onto chars with lower porosity, however to increase retention (sorption), the char is milled more finely to increase surface area. Examples of high Koc molecules are the avermectins, and anthranilic diamides. Use of such chemistries may be protective against pests that attack the root and lower stem of plants, such as the larvae (grubs) of Coleoptera. Examples are Japanese beetle grubs that feed on turf roots and black vine weevil grubs that feed on the roots and lower stem of rhododendrons.

Other Components

Other components in the composition include but are not limited to, nitrogen sources, organic acids and hygroscopic substances added to yield about 4% to about 6% nitrogen by weight, and to yield about 10% to about 40% organic acids by weight, including the ranges of about 10-15%, 15-20%, 20-25%, 25-30%, 30-35% and 35-40% organic acids by weight. The amount of organic acid to add to biochar is based on the desired target pH of about 3.6 to 4.6. The amount of solutes added is measured by electrical conductivity (dS/m) as outlined in Section 04.10 of US Composting Council and USDA (2001).

Exemplary nitrogen sources include blood meal (13-0-0), bone meal (4-12-0), kelp meal (1-0-2), sodium nitrate, sulfur-coated urea, inorganic salts such as magnesium ammonium nitrate, potassium nitrate, ammonium nitrate, calcium nitrate, and the like; urea-formaldehyde reaction products, and isobutylidene diurea (IBDU).

Exemplary organic acids include calcium chelate derived from calcium chloride, 5% chelated iron derived from iron sulfate, 5% manganese chelate derived from manganese sulfate, 5% zinc chelate derived from zinc sulfate; copper (II) sulfate pentahydrate, boric acid, phosphoric acid, and sodium molybdate.

A liquid component is optionally added to the mixture during the blending step of the process to assist in granulation of the material, and to control dust. The liquid is generally added at an amount which results in no greater than 35% by weight in the granules.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Method of Making

The process for making the composition comprises the following steps:
  (a) Selection of biomass source (hardwood or monocot sources) for optimum porosity characteristics, generally in the range of 150 to 250 µm; alternatively softwood biomass may be utilized (generally in the range of 10 to 65 µm diameter tracheids) for loading molecules which have higher affinities to carbon.
  (b) Biomass with variable pore sizes (vessel diameters) may be blended to yield a product mix with variable adsorptive characteristics, where biomass with larger internal pores are used to internally load (absorb) the desired molecule, and those with smaller internal diameters for adsorptive loading of the selected molecule;
  (c) mechanically milling agricultural biomass for optimal size characteristics, generally ranging from 2000 to 4760 microns; where biomass with smaller internal diameters are milled finer and those which have greater porosity may be milled coarser.
  (d) screened to remove oversized and undersized particles (the improperly sized material is optionally milled to the appropriate size and rescreened);
  (e) appropriately sized agricultural biomass composition is blended with a nitrogen source and an organic acid;
  (f) blended composition is loaded with the active agent,
  (g) mixture is tumbled for even distribution to allow solute sorption onto the previously prepared biomass
  (h) the mixture is dried to about 10% to about 15% moisture content In specific embodiments, the final composition has a bulk density of less than about 40 pounds per cubic foot with <20% wt moisture.

In some embodiments, the active agent in the form of a liquid is applied to the agricultural biomass granules. In this embodiment, the active agent is first dissolved in a solvent to form a concentrated solution which is first solubilized using appropriate solvents and/or surfactants. The product is tumbled for about 20 to 30 minutes to evenly distribute the active agent on to the agricultural biomass composition, and dried to about 10% to about 15% moisture content. Moisture content is determined as percent of total mass, using AOAC method 2.2.01.

In another embodiment the active agent in powder form is optionally intermixed with the agricultural biomass to form the agricultural biomass composition. Without intending to be bound to a particular theory, electrostatic forces are believed to be operative to retain active agent powder in contact with the granules of the agricultural biomass. The active agent granules are optionally of a mean size less than 20 percent that of the mean agricultural biomass granule size. Optionally, active agent powder is sized such that the powder grain diameter has a mean particle diameter of less than 10% that of the agricultural biomass granules mean size. Optionally, the active agent powder has a mean diameter of less than 2% that of the agricultural biomass granules particle diameter.

Method of Use

In one embodiment the invention provides a method for minimizing leaching of an active ingredient into water sources. The composition impregnated with the active agent effectively reduces the leaching of and facilitates the metering of the active agent. The composition is administered volumetrically (teaspoon, tablespoon, cup, shaker, spreader), or applied topically by Hudson Bak-Pak Applicator (Model 18539, by Ariens Specialty Brands, LLC), Stihl back pack/duster (SR430 or SR400, by Stihl USA) or by Vortex SPC Spreader (Vortex granular Systems, LLC distributed by John Deere Landscapes), or by weight (biodegradable packet) or by soil implantation with an insertion tool to an environmental area comprising the soil or root zone in which plants grow, typically within the top 12" of the soil surface. For example, the composition may be inserted into the soil/root zone via Vertimulcher (such as the Webster Vertimulcher Model TC300 distributed by MK Rittenhouse and Sons, LTD). The composition may optionally be applied to the root ball from which roots are expected to emerge upon planting. Alternatively, the composition is mixed with the soil media in which plants are potted and grown. Product application is to be applied at the per acre limit rate. For example, imidacloprid applied to soil is limited to 0.4 lb (182 grams active ingredient) per acre per year. For applications to the soil, 1.0 to 1.5 GAI per inch diameter breast height (DBH) may be applied for piercing sucking or coleopteran pests of trees. For shrub applications, the rates are similar, but specified per foot of shrub height. This same rate will treat a 3 gallon-sized nursery potted plant.

In another embodiment the invention provides a method for release of an active agent from the composition in a controlled manner. In yet another embodiment the agricultural biomass composition impregnated with about 5% wt to about 45% wt of an active agent releases the active agent at a rate in the range of about 10 mg/L to about 500 mg/L, more preferably at a rate of about 33 mg/L.

In one other embodiment the invention provides a method for release of an active agent from the agricultural biomass composition immediately.

In yet one another embodiment the invention provides a method for release of some of the active agent from the agricultural biomass composition immediately followed by the release of the rest of the active agent in a controlled release manner.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

General Information

BioChar was purchased from Charcoal House, LLC, Crawford, Nebr.

Blood meal was purchased from Ohio Earth Food, Hartville, Ohio.

Chelated calcium was purchased from Baicor, LLC, Logan, Utah.

Imidacloprid was purchased from Bayer CropScience, Triangle Park, N.C.

Azadirachtin was purchased from Soluneem Inc., Sausalito, Calif.

Thiabendazole was purchased from Syngenta CropScience, Greensboro, N.C.

Dinotefuran was purchased from Valent, USA Longwood, Fla.

Nitroform was purchased from Ureaform, GreenwayBiotech, Inc.

*Ascophyllum nodosum* was purchased from Ohio Earth Food, Hartville, Ohio.

Strobulurin was purchased from Bayer CropScience, Triangle Park, N.C.

Paclobutrazol was purchased from Syngenta CropScience, Greensboro, N.C.

Abamectin was purchased from Syngenta CropScience, Greensboro, N.C.

Acephate was purchased from United Phosphorous, Inc. Trenton, N.J.

Triadimefon was purchased from Bayer Environmental Science, RTP, N.C.

Ethephon was purchased from Bayer CropScience, Research Triangle Park, N.C.

Testing Methods

Moisture content is determined as percent of total mass, dry basis was determined in accordance with ASTM D1762-84 or, Moisture content was determined as percent of total mass, using AOAC method 2.2.01.

Particulate size of the final product is determined by dry sieving as outlined in ASTM D2862-10.

Organic carbon, where Class 1: ≥60%, Class 2: ≥30% and <60%, and Class 3: ≥10% and <30%, % of total mass, was determined in accordance with ASTM D4373-02.

Total nitrogen, as % of total mass, was determined by combustion-IR detection.

pH was measured as outlined in Section 04.11 of US Composting Council and USDA (2001) was determined by sample equilibration methods described in Rajkovich et al. (2011) *Biol. Fertil. Soils,* 48(3): 271-284.

Electrical conductivity (dS/m) as outlined in Section 04.10 of US Composting Council and USDA (2001) was determined by sample equilibration methods described in Rajkovich et al. (2011) *Biol. Fertil. Soils,* 48(3): 271-284.

Liming (if pH is >7.0) as % $CaCO_3$ as outlined in Rajkovich et al. (2011).

Particle size distribution % <420 μm; %2380 μm, % >4760 μm by dry sieving as outlined in ASTM D2862-10 method for activated carbon.

The ability of the particles to disperse in water can be measured in a water dispersability test. The test involves placing about 10 grams of the granular material into 100 ml of water at room temperature in a closed glass container. The container is then inverted and the time is observed until the material completely disperses. After every minute, the container is inverted. The products of the present invention optionally have a dispersability time of less than 3 minutes.

Example 1: Biochar Impregnated with Imidacloprid

Technical grade imidacloprid (10.1 kg) was first solubilized in 7.1 kg dimethylsulfoxide and 12.8 g tetrahydrofurfuryl alcohol to form a liquid concentrate. The liquid concentrate was mixed at ambient temperatures in an inert vessel under negative atmosphere.

Separately bioChar (Class 1) was passed through a No. 4 (4760 μm) screen and in one form 33 kg was blended with 5 kg of chelated Calcium (an organic acid) to which, 32 kg blood meal as an organic source of nitrogen was added and blended. To the resulting biochar blend was added the imidacloprid liquid concentrate and the resulting mixture was thoroughly blended by tumbling until the active agent was evenly distributed on the organic matrices, then dried. Product samples were taken and inspected by microscopy for quality control. The biochar end product provides 10 grams active ingredient imidacloprid/100 g and 4 g nitrogen/100 g of biochar product having 19.9% wt moisture and a bulk density of ~36.6 cu ft. Total nitrogen, as % of total mass, is determined by combustion-IR detection.

Biochar impregnated with other active agents, such as, dinotefuran, azadirachtin, thiabendazole, strobulurin, paclobutrazol, abamectin, acephate or ethephon, were prepared using the procedure described above.

BioChar was passed through a ¼" (6350 μm) screen and in one form the biochar product comprises 60% wt monocot biochar; 15% wt chelated calcium and provides 5% to 25% by weight insecticidal dinotefuran.

BioChar was passed through a No. 10 (2000 μm) screen and in one form 40 to 60% by wt was blended with organic nitrogen alternatively a bio-stimulant such as *Ascophyllum nodosum* and to which an organic acid was added, onto which the insect growth regulator, azadirachtin was blended in from 5 to 25% by weight.

BioChar was passed through a ¼" screen and in one form 50 to 60% by weight was blended with a systemic fungicide such as thiabendazole or triadimefon to which slow release nitrogen alternatively a bio-stimulant such as *Ascophyllum nodosum* and an organic acid was blended from 5 to 30% by weight.

BioChar was passed through a No. 4 (4760 μm) screen and in one form 25 to 65% by wt was blended with an organic nitrogen alternatively a bio-stimulant such as *Ascophyllum nodosum* and an organic acid, onto which a contact fungicide, such as a strobulurin was blended.

BioChar was passed through a No. 10 (2000 μm) screen and in one form 40 to 60% by wt was blended with a plant growth regulator, such as paclobutrazol to which an organic acid has been blended.

BioChar was passed through a ¼" screen (6350 μm) and in one form 60% by weight was blended with a contact insecticide such as abamectin to which slow release nitrogen, alternatively a bio-stimulant such as *Ascophyllum nodosum* and organic acid was blended.

Example 2: Treatment of Ornamental Peppers with Biochar Impregnated with Insecticides Ornamental peppers in 6 inch pots infested with a mean of 8.36 green aphids per leaf were maintained in an indoor greenhouse and grown under high intensity (1000 W) metal halide grow lamps. To each of 7 pots was added 1 teaspoon of (i) biochar impregnated with 5% (w/w) acephate prepared as described in Example 1 (ii) biochar impregnated with 5% (w/w) imidacloprid prepared as described in Example 1 (iii) biochar alone or (iv) ArborChar Tree and Shrub fertilizer and the treatments were watered in. On day 7 following treatment, the number of live aphids on the foliage of each plant was counted (dead aphids that fell to the soil were not counted). As early as 2 days after treatment dead aphids were observed. Table 1 gives the number of live aphids on day 7. The values are reported as means with 95% confidence intervals.

TABLE 1

| Treatment | Number of live aphids on Day 7 following treatment |
|---|---|
| 5% (w/w) acephate Biochar | 1.07 ± 0.5 |
| 5% (w/w) imidacloprid Biochar | 0.8 ± 0.3 |
| Biochar | 12.4 ± 1.7 |
| ArborChar Tree and Shrub fertilizer | 11.4 ± 2.3 |

The ornamental pepper plants treated with the biochar impregnated compositions had statistically significant lower numbers of aphids compared to the plants treated with biochar or the ArborChar Tree and Shrub fertilizer. The reduction in the mean number of aphids shows that the active ingredient leaches out of the impregnated biochar composition.

Example 3: Treatment of Arugula with Biochar Impregnated with Insecticides

Arugula in 6 inch pots infested with a mean of 7.8 green aphids per leaf were maintained in an indoor greenhouse and grown under high intensity (1000 W) metal halide grow lamps. To each of 10 pots was added either 1 teaspoon of biochar impregnated with 5% (w/w) dinotefuran and the treatment were watered in or the plants were untreated. On day 2 following treatment, the number of live aphids on the foliage of each plant was counted (dead aphids that fell to the soil were not counted). Table 2 gives the percent mortality of aphids on day 2. The values are reported as means with 95% confidence intervals.

TABLE 2

| Treatment | % Mortality on Day 2 following treatment |
|---|---|
| 5% w/w dinotefuran biochar | 79.6 ± 9.3 |
| Untreated | 3.0 ± 2.1 |

The arugula plants treated with the biochar impregnated compositions had statistically significant lower numbers of aphids compared to the untreated plants. The increased mortality of the aphids shows that the active ingredient leaches out of the impregnated Biochar composition.

Example 4: Treatment of Ornamental Peppers with Biochar Impregnated with Insecticides Ornamental peppers in 6 inch pots infested with a mean of 9.86 green aphids per leaf were maintained in an indoor greenhouse and grown under high intensity (1000 W) metal halide grow lamps. To each of 7 pots was added 1 teaspoon of (i) biochar impregnated with 5% (w/w) dinotefuran prepared as described in Example 1 (ii) biochar impregnated with 25% (w/w) azadirachtin prepared as described in Example 1 or (iii) no treatment and the treatments were watered in. On day 5 following treatment, the number of live aphids on the foliage of each plant was counted (dead aphids that fell to the soil were not counted). As early as 2 days after treatment dead aphids were observed. Table 3 gives the number of live aphids on day 5. The values are reported as means with 95% confidence intervals.

TABLE 3

| Treatment | Average Number of live aphids on Day 5 following treatment |
|---|---|
| 5% (w/w) dinotefuran Biochar | 0.14 ± 0.1 |
| 25% (w/w) azadirachtin Biochar | 0.43 ± 0.2 |
| No treatment | 1.8 ± 0.3 |

The ornamental pepper plants treated with the biochar impregnated compositions had statistically significant lower numbers of aphids compared to the untreated plants. The reduction in the mean number of aphids shows that the active ingredient leaches out of the impregnated biochar composition.

Example 5: Biochar Impregnated with Imidacloprid—Modified Formulation

Technical grade imidacloprid was first solubilized in tetrahydrofurfuryl alcohol (THFA) to yield a 15% w/w soluble liquid (SL) of low viscosity. Separately hardwood biochar was milled fine and sieved. 98.9% of the biochar which passed through a No. 4 (4760 μm) mesh, and 68.1% passing through a No. 10 (2000 μm) mesh, was then acid washed with 10 g/100 g of 5% calcium chelate solution and 20 g/100 g Nitroform (Ureaform, GreenwayBiotech, Inc.); followed by the addition of the imidacloprid solution (5% w/w) and mixed thoroughly to allow the imidacloprid to be adsorbed. The resulting product (biochar impregnated with 5% (w/w) imidacloprid was placed in a sealed container and set aside for 24 hours at ambient temperatures to allow time for complete absorption to occur. The product was then dried to allow 1.25% by weight moisture loss.

Biochar impregnated with other active agents, such as, dinotefuran, triadimefon, and ethephon, were prepared using the procedure described above

Example 6: Leaching of Active Agents from Biochar Products

The evaluation was conducted comparing the leaching of the active agent used alone in its off the shelf solution as compared to leaching of the active agent from the formulated blended biochar products. The active agents were either blended with biochar or were used off the shelf. Dinotefuran was blended as formulated (5% w/w) on biochar or was applied as is as 5% solution. Ethephon as a soluble liquid was either blended with biochar (11.6% wt/wt) or used as is as an 11.7% solution. Triadimefon, a viscous flowable liquid, was either blended with char at 43% (w/w) or used as is. Imidacloprid 5% (w/w) was blended with biochar as described in Example 5 or used as a 5% solution To a 30 cm column of coarse sand (a "soil" with very low cation exchange capacity (CEC)) was added the test substance as listed in Table 4. 3×500 mL of artificial rain solution of 0.01 M $CaCl_2$ was applied by slow drip and the effluent was analyzed for the active agent. Table 4 summarizes the results for runs of 500 mL each.

TABLE 4

| Run No. | Test Substance | mg/L | Test Substance | mg/L |
|---|---|---|---|---|
| 1 | 11.6% (w/w) Ethephon Biochar | ND | 11.6% (w/w) Ethephon | 1896 |
| 2 | 11.6% (w/w) Ethephon Biochar | 7315 | 11.6% (w/w) Ethephon | 8200 |
| 3 | 11.6% (w/w) Ethephon Biochar | 39886 | 11.6% (w/w) Ethephon | 30629 |
|   | Mean: | 5733 |   | 13575 |
| 1 | 5% (w/w) Dinotefuran Biochar | 1066 | 5% (w/w) Dinotefuran | 954 |
| 2 | 5% (w/w) Dinotefuran Biochar | 1167 | 5% (w/w) Dinotefuran | 485 |
| 3 | 5% (w/w) Dinotefuran Biochar | 42 | 5% (w/w) Dinotefuran | 39 |
|   | Mean | 758 |   | 492 |
| 1 | 42.8% (w/w) Triadimefon Biochar | 177 | 42.8% (w/w) Triadimefon | 114 |
| 2 | 42.8% (w/w) Triadimefon Biochar | 620 | 42.8% (w/w) Triadimefon | 667 |
| 3 | 42.8% (w/w) Triadimefon Biochar | 661 | 42.8% (w/w) Triadimefon | 669 |
|   | Mean | 486 |   | 483 |
| 1 | 5% (w/w) Imidacloprid Biochar | 34.34 | 5% (w/w) Imidacloprid | 69.86 |
| 2 | 5% (w/w) Imidacloprid Biochar | 30.89 | 5% (w/w) Imidacloprid | 72.136 |
| 3 | 5% (w/w) Imidacloprid Biochar | 33.44 | 5% (w/w) Imidacloprid | 72.976 |
|   | Mean | 32.9 |   | 71.7 |

Table 4 shows that for ethephon the biochar blended and unblended formulations had a mean recovery of 15,733 and 13,575 mg/L, a 1.2 fold great recovery for the biochar product. For the dinotefuran biochar blend the recovery was 758 mg/L compared to 492 mg/L for the unmodified formulation, a 1.2 fold great recovery for the biochar product.

Triadimefon had an overall recovery of 486 mg/L and 483 mg/L for the biochar blended and unblended formulations, respectively.

For imidacloprid, the impregnated biochar and unblended formulations had a mean recovery of 32.9 mg/L and 71.7 mg/L respectively. Leaching loss was reduced by 45.8%. The results indicate that the key factors that influence leaching are water solubility and carbon absorption (Koc) which drives the selection and modification of the biochar matrix.

Various modifications of the present invention, in addition to those shown and described herein, will be apparent to those skilled in the art of the above description. Such modifications are also intended to fall within the scope of the appended claims.

It is appreciated that all materials and reagents are obtainable by sources known in the art unless otherwise specified.

All publications, including, e.g., non-patent literature, patent applications, and patents, cited in this specification are incorporated herein by reference for all purposes. The invention can be embodied in other specific forms without departing from the spirit or essential characteristics thereof.

The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A composition comprising biochar, at least one nitrogen source, at least one organic acid and at least one active agent wherein the biochar is impregnated with about 5% wt to about 45% wt of the active agent, and further wherein the biochar has a bulk density of less than about 40 pounds per cubic foot and has a size of about 90-100% passing through a ¼" mesh screen and about 50% or more passing through a 4 mesh screen; or a size of about 90-100% passing through a No. 4 mesh screen and about 70% or more passing through a No. 10 mesh screen; or a size of about 90-100% passing through a No. 10 mesh screen and about 50% or more passing through a No. 45 mesh screen.

2. The composition of claim 1, wherein the biochar comprises about 5% wt to about 75% wt of an herbaceous non-woody and/or a monocot biochar or a hardwood biochar or a softwood biochar or a combination of two or more thereof.

3. The composition of claim 2, wherein the biochar comprises about 25% wt to about 50% wt of the herbaceous, non-woody, monocot biochar and about 50% wt to about 75% wt of the hardwood biochar.

4. The composition of claim 1, wherein the biochar has a size of about 90-100% passing through a No. 4 mesh screen and about 70% or more passing through a No. 10 mesh screen.

5. The composition of claim 1, wherein the active agent is selected from the group consisting of an insecticide, an insect growth regulator, a fungicide, a plant growth regulator, a pesticide, and a bio-pesticide.

6. The composition of claim 5, wherein the insecticide is selected from the group consisting of imidacloprid, dinotefuran, acephate and abamectin; the insect growth regulator is azadirachtin; the fungicide is selected from the group consisting of thiabendazole, triadimefon and a strobulurin; the plant growth regulator is selected from the group consisting of paclobutrazol, ethephon and indole-3-butyric acid; and the bio-pesticide is a mixture of spinosad A and spinosad D.

7. The composition of claim 5, wherein the pesticide is selected from the group consisting of an algicide, a bacteriocide, a defoliant, a herbicide, a miticide, a nematicide and an ovicide.

8. The composition of claim 1, wherein the nitrogen source is selected from the group consisting of blood meal, bone meal, kelp meal, sodium nitrate, sulfur-coated urea, inorganic salts, urea-formaldehyde reaction products, and isobutylidene diurea.

9. The composition of claim 1, wherein the organic acid is selected from the group consisting of calcium chelate derived from calcium chloride, 5% chelated iron derived from iron sulfate, 5% manganese chelate derived from manganese sulfate, 5% zinc chelate derived from zinc sulfate, copper (II) sulfate pentahydrate, boric acid, phosphoric acid and sodium molybdate.

10. The composition of claim 1, comprising about 46% wt biochar, about 10% wt chelated calcium chloride, about 34% wt blood meal and about 10% wt technical imidacloprid.

11. The composition of claim 1, wherein the active agent is released from the biochar at a rate of 33 mg/L.

12. The composition of claim 1, where the active agent is released from the biochar in a controlled manner.

13. The composition of claim 1, wherein the active agent is released from the biochar immediately.

14. The composition of claim 1, wherein a portion of the active agent is released from the biochar immediately and the remainder of the active agent is released from the biochar in a controlled release manner.

15. The composition of claim 1, comprising biochar, chelated calcium chloride, blood meal, and imidacloprid.

16. The composition of claim 8, wherein the inorganic salts are selected from the group consisting of magnesium ammonium nitrate, potassium nitrate, ammonium nitrate and calcium nitrate.

17. A method for minimizing leaching of an active agent into water sources comprising applying to soil a composition comprising biochar, at least one nitrogen source, at least one organic acid and at least one active agent wherein the biochar is impregnated with about 5% wt to about 45% wt of the active agent, and further wherein the biochar has a bulk density of less than about 40 pounds per cubic foot and has a size of about 90-100% passing through a ¼" mesh screen and about 50% or more passing through a 4 mesh screen; or a size of about 90-100% passing through a No. 4 mesh screen and about 70% or more passing through a No. 10 mesh screen; or a size of about 90-100% passing through a No. 10 mesh screen and about 50% or more passing through a No. 45 mesh screen.

* * * * *